United States Patent
Kim et al.

(10) Patent No.: US 9,217,166 B2
(45) Date of Patent: Dec. 22, 2015

(54) D-PSICOSE 3-EPIMERASE MUTANT WITH IMPROVED THERMAL STABILITY, AND CONTINUOUS PRODUCTION OF D-PSICOSE USING SAME

(75) Inventors: Yang Hee Kim, Bucheon-si (KR); Jin Ha Kim, Bucheon-si (KR); Young Mi Lee, Bucheon-si (KR); Young Ho Hong, Gwangmyeong-si (KR); Min Hae Kim, Incheon (KR); Seong Bo Kim, Seoul (KR); Seung Won Park, Yongin-si (KR); Seung Hyun Oh, Bucheon-si (KR); Deok Kun Oh, Gwacheon-si (KR); Jin Geun Choi, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 14/240,647

(22) PCT Filed: Aug. 21, 2012

(86) PCT No.: PCT/KR2012/006637
§ 371 (c)(1),
(2), (4) Date: Feb. 24, 2014

(87) PCT Pub. No.: WO2013/027999
PCT Pub. Date: Feb. 28, 2013

(65) Prior Publication Data
US 2014/0199732 A1  Jul. 17, 2014

(30) Foreign Application Priority Data
Aug. 24, 2011  (KR) .................... 10-2011-0084712

(51) Int. Cl.
C12P 19/02 (2006.01)
C12P 19/24 (2006.01)
C12N 9/90 (2006.01)

(52) U.S. Cl.
CPC . C12P 19/24 (2013.01); C12N 9/90 (2013.01); C12P 19/02 (2013.01); C12Y 501/03 (2013.01)

(58) Field of Classification Search
CPC combination set(s) only.
See application file for complete search history.

(56) References Cited

U.S. PATENT DOCUMENTS 8,030,035 B2 * 10/2011 Oh et al. .................... 435/94
2010/0190225 A1  7/2010 Oh et al.
2012/0244580 A1  9/2012 Hung et al.

FOREIGN PATENT DOCUMENTS

| KR | 10-2006-0125971 A | 12/2006 |
| KR | 10-0744479 B1 | 8/2007 |
| KR | 10-2011-0035805 A | 4/2011 |
| WO | 2011/040708 A2 | 4/2011 |

OTHER PUBLICATIONS

Characterization of an *Agrobacterium tumefaciens* D-psicose 3-epimerase that converts D-fructose to D-psicose Kim, Hye-Jung; et al Applied and Environmental Microbiology (2006), 72(2), 981-985.*

Kim, Hye-Jung (Roles of Ile66 and Ala107 of D-psicose 3-epimerase from *Agrobacterium tumefaciens* in binding 06 of its substrate, D-fructose. Biotechnol Lett (2010) 32:113-118.*

Choi et al., "Improvement in the Thermostability of D-Psicose 3-Epimerase from *Agrobacterium tumefaciens* by Random and Site-Directed Mutagenesis," *Applied and Environmental Microbiology* 77(20):7316-7320, Oct. 2011.

Choi et al., "Improvement of Thermostability of D-psicose 3-epimerase from *Agrobacterium tumefaciens* by Random and Site-directed mutagenesis," PEE23, KSBB, Abstracts of Current Biotechnology and Bioengineering(XXVIII): Apr. 2011, p. 176.

Matsuo et al., "Dietary D-psicose, a C-3 epimer of D-fructose, suppresses the activity of hepatic lipogenic enzymes in rats," *Asia Pacific J Clin Nutr* 10(3):233-237, 2001.

Matsuo et al., "D-Psicose, a rare sugar that provides no. energy and additionally beneficial effects for clinical nutrition," ICCN Poster Presentations, *Asia Pacific Journal of Clinical Nutrition* 13(Suppl):S127, 2004.

* cited by examiner

*Primary Examiner* — Kagnew H Gebreyesus
(74) *Attorney, Agent, or Firm* — Seed IP Law Group PLLC

(57) ABSTRACT

The present invention relates to a D-psicose 3-epimerase variant with improved thermostability by substituting an amino acid at a specific position of an amino acid sequence of a wild type D-psicose 3-epimerase. Further, the present invention provides a recombinant expression vector including a gene of the D-psicose 3-epimerase variant, and a recombinant strain transformed with the recombinant expression vector. Furthermore, the present invention provides an immobilized reactor prepared using the D-psicose 3-epimerase variant or the recombinant strain, and a method of continuously producing D-psicose using the immobilized reactor.

14 Claims, 2 Drawing Sheets

SEQUENCE LISTING

```
<160> NUMBER OF SEQ ID NOS: 1

<210> SEQ ID NO 1
<211> LENGTH: 289
<212> TYPE: PRT
<213> ORGANISM: Artificial Sequence
<220> FEATURE:
<223> OTHER INFORMATION: D-psicose 3-epimerase from Agrobacterium
      tumefaciens

<400> SEQUENCE: 1

Met Lys His Gly Ile Tyr Tyr Ser Tyr Trp Glu His Glu Trp Ser Ala
 1               5                  10                  15

Lys Phe Gly Pro Tyr Ile Glu Lys Val Ala Lys Leu Gly Phe Asp Ile
             20                  25                  30

Ile Glu Val Ala Ala His His Ile Asn Glu Tyr Ser Asp Ala Glu Leu
         35                  40                  45

Ala Thr Ile Arg Lys Ser Ala Lys Asp Asn Gly Ile Ile Leu Thr Ala
     50                  55                  60

Gly Ile Gly Pro Ser Lys Thr Lys Asn Leu Ser Ser Glu Asp Ala Ala
 65                  70                  75                  80

Val Arg Ala Ala Gly Lys Ala Phe Phe Glu Arg Thr Leu Ser Asn Val
                 85                  90                  95

Ala Lys Leu Asp Ile His Thr Ile Gly Gly Ala Leu His Ser Tyr Trp
            100                 105                 110

Pro Ile Asp Tyr Ser Gln Pro Val Asp Lys Ala Gly Asp Tyr Ala Arg
            115                 120                 125

Gly Val Glu Gly Ile Asn Gly Ile Ala Asp Phe Ala Asn Asp Leu Gly
        130                 135                 140

Ile Asn Leu Cys Ile Glu Val Leu Asn Arg Phe Glu Asn His Tyr Leu
145                 150                 155                 160

Asn Thr Ala Ala Glu Gly Val Ala Phe Val Lys Asp Val Gly Lys Asn
                165                 170                 175

Asn Val Lys Val Met Leu Asp Thr Phe His Met Asn Ile Glu Glu Asp
            180                 185                 190

Ser Phe Gly Asp Ala Ile Arg Thr Ala Gly Pro Leu Leu Gly His Phe
        195                 200                 205

His Thr Gly Glu Ser Asn Arg Arg Val Pro Gly Lys Gly Arg Met Pro
    210                 215                 220

Trp His Glu Ile Gly Leu Ala Leu Arg Asp Ile Asn Tyr Thr Gly Ala
225                 230                 235                 240

Val Ile Met Glu Pro Phe Val Lys Thr Gly Gly Thr Ile Gly Ser Asp
                245                 250                 255

Ile Lys Val Trp Arg Asp Leu Ser Gly Gly Ala Asp Ile Ala Lys Met
            260                 265                 270

Asp Glu Asp Ala Arg Asn Ala Leu Ala Phe Ser Arg Phe Tyr Leu Gly
        275                 280                 285

Gly
```

D-PSICOSE 3-EPIMERASE MUTANT WITH IMPROVED THERMAL STABILITY, AND CONTINUOUS PRODUCTION OF D-PSICOSE USING SAME

CROSS-REFERENCE TO RELATED APPLICATIONS

This application is a U.S. national stage application filed under 35 U.S.C. § 371of International Patent Application PCT/KR2012/006637, accorded an international filing date of Aug. 21, 2012, which claims the benefit of Korean (KR) Application No. 10-2011-0084712 filed Aug. 24, 2011.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200198_407USPC_SEQUENCE_LISTING.txt. The text file is 2.9 KB, was created on Sep. 17, 2015, and is being submitted electronically via EFS-Web.

TECHNICAL FIELD

The present invention relates to a D-psicose 3-epimerase variant with improved thermostability derived from *Agrobacterium tumefaciens* and a method of producing D-psicose using the same.

BACKGROUND ART

D-psicose is a monosaccharide known as a rare sugar because it is rarely found in natural materials or is present in small amounts. D-psicose has an ultralow energy density and a sweet taste similar to sugar, and thus is widely used as a functional sweetener.

D-psicose is an epimer of fructose and has a degree of sweetness and taste very similar to fructose. However, unlike fructose, D-psicose is scarcely metabolized in the body and thus has almost zero-calories. D-psicose can be used as an effective ingredient for diet foods since D-psicose has capabilities in inhibiting activity of an enzyme involved in lipid synthesis and reducing abdominal obesity. Further, sugar alcohols such as xylitol and the like that are widely used as sugar substitute may have side effects such as causing diarrhea in case of over consumption. On the contrary, D-psicose is known to have substantially no side effects (Matsue, T., Y. Baba, M. Hashiguchi, K. Takeshita, K. Izumori, and H. Suzuki. 2001. Dietary D-psicose, a C-3 epimer of D-fructose, suppresses the activity of hepatic lipogenic enzymes in rats. Asia Pac. J. Clin. Nutr. 10:233-237; Matsuo, T., and K. Izumori. 2004. D-psicose, a rare sugar that provides no energy and additionally beneficial effects for clinical nutrition. Asia Pac. J. Clin. Nutr. 13:S127).

For such a reason, D-psicose draws keen attention as a diet sweetener, and there is a growing need for development of a method for effectively producing D-psicose in the food industry. As the necessity for developing D-psicose has been raised, many researches for producing D-psicose from fructose using the conventional biological methods have been performed. As enzymes capable of converting fructose into D-psicose, D-psicose 3-epimerase derived from *Agrobacterium tumefaciens* and D-tagatose 3-epimerase derived from *Pseudomonas cichorii* or *Rhodobacter sphaeroides* are known. D-psicose 3-epimerase is known to have higher activity than D-tagatose 3-epimerase.

Strains belonging to genus *Corynebacterium* are industrial microorganisms which produce chemical materials including L-lysine, L-threonine and various nucleic acids having diverse usages in feed forage, pharmaceuticals, foods, and the like. Such strains of genus *Corynebacterium* are GRAS (Generally Recognized As Safe) strains, and have properties that are easy to be genetically engineered and mass cultured. Moreover, genus *Corynebacterium* strains have high stability under various process conditions and a relatively strong cell membrane structure as compared with other bacteria. For these reasons, the strains have biological properties that the bacterial cells exist in a stable state under high osmotic pressure owing to high sugar concentration and the like.

PRIOR ART DOCUMENTS

1) Korean Patent No. 10-0744479 B1 (published on Aug. 1, 2007)
2) Korean Patent Publication No. 10-2011-0035805A (published on Apr. 6, 2011)

DISCLOSURE

Technical Problem

The present inventors became aware of the problems of D-psicose 3-epimerase derived from *Agrobacterium tumefaciens* that has poor utility due to low thermostability despite high activity, and developed a D-psicose 3-epimerase variant with improved thermostability such that D-psicose currently drawing high attention as an important food material can be produced industrially on a large scale, thereby providing a method of continuously producing D-psicose using such a variant. Based on such research, the present inventors have arrived at the present invention.

Specifically, the present invention is aimed at providing a D-psicose 3-epimerase variant with improved thermostability by substituting an amino acid at a specific position of an amino acid sequence of a wild type D-psicose 3-epimerase.

One embodiment of the present invention is also aimed at providing a recombinant expression vector including a gene of the D-psicose 3-epimerase variant and a recombinant strain transformed with the recombinant expression vector.

Further, the present invention is aimed at providing a packed bed reactor prepared using the immobilized D-psicose 3-epimerase variant or the recombinant strain, and a method of continuously producing D-psicose using the immobilized reactor.

Technical Solution

The present invention provides a D-psicose 3-epimerase variant with improved thermostability by substituting an amino acid at a specific position of an amino acid sequence of a wild type D-psicose 3-epimerase. Further, the present invention provides a recombinant expression vector including a gene of the D-psicose 3-epimerase variant, and a recombinant strain transformed with the recombinant expression vector. Furthermore, the present invention provides an immobilized reactor prepared using the D-psicose 3-epimerase variant or the recombinant strain, and a method of continuously producing D-psicose using the immobilized reactor.

More specifically, one embodiment of the present invention provides a D-psicose 3-epimerase variant with improved thermostability, wherein the variant is a variant of a wild type D-psicose 3-epimerase derived from *Agrobacterium tumefaciens* and has an amino acid sequence in which isoleucine (Ile) at position 33 of the amino acid sequence is substituted with an amino acid selected from the group consisting of leucine (Leu), cysteine (Cys) and valine (Val), or an amino acid sequence in which serine (Ser) at position 213 of the amino acid sequence is substituted with cysteine.

Another embodiment of the present invention provides a D-psicose 3-epimerase variant with improved thermostability, wherein the variant is a variant of a wild type D-psicose 3-epimerase derived from *Agrobacterium tumefaciens* and has an amino acid sequence in which isoleucine (Ile) at position 33 of the amino acid sequence is substituted with an amino acid selected from the group consisting of leucine (Leu), cysteine (Cys) and valine (Val), and serine (Ser) at position 213 of the amino acid sequence is substituted with cysteine.

Yet another embodiment of the present invention provides a recombinant expression vector including a gene encoding the D-psicose 3-epimerase variant.

Yet another embodiment of the present invention provides *Corynebacterium glutamicum* pFIS-1-ATPE-2 transformed with the recombinant expression vector.

Yet another embodiment of the present invention provides a method of producing D-psicose from fructose using the D-psicose 3-epimerase variant.

Yet another embodiment of the present invention provides a method of producing D-psicose from fructose using the recombinant *Corynebacterium glutamicum* pFIS-1-ATPE-2.

Yet another embodiment of the present invention provides an immobilized reactor for producing D-psicose, comprising a column filled with a bead to which the D-psicose 3-epimerase variant is immobilized.

Yet another embodiment of the present invention provides a method of producing D-psicose by introducing a fructose solution into the immobilized reactor.

Advantageous Effects

The present invention provides a D-psicose 3-epimerase variant in which an amino acid at a specific position of an amino acid sequence of a wild type D-psicose 3-epimerase is substituted. The D-psicose 3-epimerase variant has advantages in that the variant has significantly improved thermostability while maintaining enzymatic activity, thereby allowing D-psicose currently drawing high attention as important food materials to be more effectively and industrially produced at large scale.

Specifically, the D-psicose 3-epimerase variant according to the present invention has a remarkably extended half-life at general enzyme reaction temperature as compared with a wild type D-psicose 3-epimerase, thereby allowing the prepared D-psicose 3-epimerase to be used for a long time in the production of D-psicose. Therefore, the D-psicose 3-epimerase variant according to the present invention may reduce production time and cost, thereby improving production efficiency.

Further, the present invention provides a recombinant vector for use in expressing the D-psicose 3-epimerase variant, and a recombinant strain, *Corynebacterium glutamicum* pFIS-1-ATPE-2 transformed with the recombinant expression vector. Therefore, the present invention has advantages in that providing a method for continuously producing D-psicose on a large scale by forming an immobilized reactor using the D-psicose 3-epimerase variant or the recombinant strain.

MODE FOR INVENTION

Figure 1:
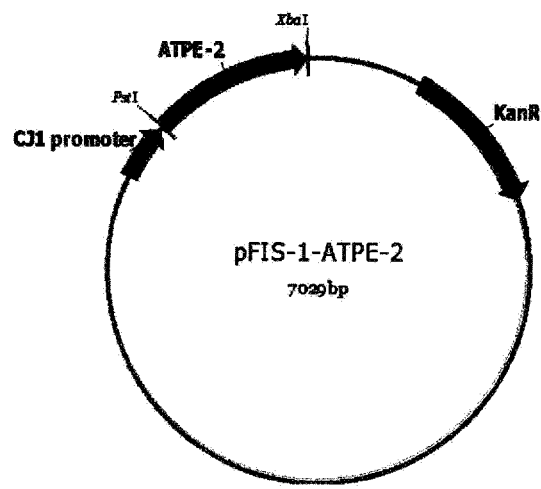
FIG. 1 depicts a recombinant expression vector including a D-psicose 3-epimerase variant gene derived from *Agrobacterium tumefaciens*.

The present invention provides a D-psicose 3-epimerase variant with improved thermostability by substituting an amino acid at a specific position of an amino acid sequence of a wild type D-psicose 3-epimerase. Further, the present invention provides a recombinant expression vector including a gene of the D-psicose 3-epimerase variant, and a recombinant strain transformed with the recombinant expression vector. Furthermore, the present invention provides an immobilized reactor prepared using the D-psicose 3-epimerase variant or the recombinant strain, and a method of continuously producing D-psicose using the immobilized reactor.

Hereinafter, embodiments of the present invention will be described in more detail. Descriptions of details apparent to a person having ordinary knowledge in the art or relevant field will be omitted herein.

One embodiment of the present invention provides a D-psicose 3-epimerase variant with improved thermostability, wherein the variant is a variant of a wild type D-psicose 3-epimerase derived from *Agrobacterium tumefaciens* and has an amino acid sequence in which isoleucine (Ile) at position 33 of the amino acid sequence is substituted with an amino acid selected from the group consisting of leucine (Leu), cysteine (Cys) and valine (Val), or an amino acid sequence in which serine (Ser) at position 213 of the amino acid sequence is substituted with cysteine.

The *Agrobacterium tumefaciens* is a well known strain, and *Agrobacterium tumefaciens* ATCC 33970 may be used as an example.

The wild type D-psicose 3-epimerase derived from *Agrobacterium tumefaciens* has an amino acid sequence of SEQ ID NO: 1 in Korean Patent Publication No. 10-2011-0035805A or a functional fragment thereof. As used herein, the term "functional fragment" may refer to a fragment including mutations due to a substitution, an insertion or a deletion of partial amino acids in the amino acid sequence of SEQ ID NO: 1 and having an activity of converting fructose to D-psicose.

The D-psicose 3-epimerase variant refers to an enzyme having an amino acid sequence in which an amino at a specific position of the amino acid sequence of a wild type D-psicose 3-epimerase derived from *Agrobacterium tumefaciens* is substituted.

More preferably, the D-psicose 3-epimerase variant represents that isoleucine at position 33 of the amino acid sequence is substituted with leucine.

Another embodiment of the present invention provides a D-psicose 3-epimerase variant with improved thermostability, wherein the variant has an amino acid sequence in which isoleucine (Ile) at position 33 of the amino acid sequence is substituted with an amino acid selected from the group consisting of leucine (Leu), cysteine (Cys) and valine (Val), and serine (Ser) at position 213 of the amino acid sequence is substituted with cysteine.

More preferably, the D-psicose 3-epimerase variant represents that isoleucine at position 33 of the amino acid sequence is substituted with leucine, and serine at position 213 of the amino acid sequence is substituted with cysteine.

Yet another embodiment of the present invention provides a recombinant expression vector including a D-psicose 3-epimerase variant gene (FIG. 1).

Yet another embodiment of the present invention provides *Corynebacterium glutamicum* pFIS-1-ATPE-2 transformed with the recombinant expression vector.

The recombinant strain *Corynebacterium glutamicum* pFIS-1-ATPE-2 was deposited as accession number KCCM 11204P at KCCM (Korean Culture Center of Microorganisms) located at Hongje 1-dong, Seodaemun-ku, Seoul, Korea on Aug. 18, 2011 in accordance with the Budapest Treaty.

Yet another embodiment of the present invention provides a method of producing D-psicose from fructose using the D-psicose 3-epimerase variant or the recombinant *Corynebacterium glutamicum* pFIS-1-ATPE-2.

Yet another embodiment of the present invention provides an immobilized reactor for producing D-psicose comprising a column filled with a bead to which the D-psicose 3-epimerase variant or the recombinant *Corynebacterium glutamicum* pFIS-1-ATPE-2 is immobilized.

The term "immobilized reactor" refers to a reactor in which the reaction for producing D-psicose is performed by a strain encapsulated in alginate bead, or through a column filled with a strain or an enzyme encapsulated in alginate bead. Namely, the immobilization means that a substance providing a biological activity, in this case, D-psicose 3-epimerase or a strain including the same is immobilized on a carrier.

As the carrier for immobilizing the enzyme variant or the recombinant strain, any carriers capable of being used for immobilization of enzymes or strains in the related art may be used without limitation. Preferably, sodium alginate may be used.

Sodium alginate is a natural colloidal polysaccharide abundantly occurring in cell membranes of seaweed and consists of β-D-mannuronic acid and α-L-guluronic acid. Sodium alginate forms beta-1,4-bonding randomly in terms of content and may be advantageously used for stable immobilization of strains or enzymes.

Yet another embodiment of the present invention provides a method of producing D-psicose by introducing a fructose solution into the immobilized reactor.

The term "half-life" as used herein refers to a period that is taken for the relative activity of initial enzyme reaction of an enzyme or an enzyme variant to be reduced to 50, when the relative activity of initial enzyme reaction of the enzyme or enzyme variant is assumed to be 100.

The term "operation stability" as used herein refers to a state that a reactor may be operated maintaining suitable productivity to continuously produce a desired product (in the present invention, D-psicose) as compared with initial activity. The operation stability is usually represented by an operational time (time unit and the like).

Hereinafter, the present invention will be described in more detail with reference to the following examples and comparative examples. It should be understood that these examples are provided for illustration only and are not to be construed in any way as limiting the scope of the present invention.

Measurement of D-Psicose 3-Epimerase Activity

The activity of D-psicose 3-epimerase was measured using fructose as a substrate. D-psicose 3-epimerase or a sample comprising D-psicose 3-epimerase was added to 50 mM PIPES (piperazine-N,N'-bis(2-ethanesulfonic acid)) buffer solution containing 20 mM of substrate, pH 8.0, followed by reacting at 50° C. for 10 minutes. To the reacted solution, hydrochloric acid was added so that the final concentration is 200 mM to stop the reaction. The concentration of fructose and D-psicose was measured using an HPLC equipped with an RI (Refractive Index) detector. The HPLC analysis was performed under the condition that a sample was injected to a column set to 80° C. (BP-100 $Ca^{2+}$ carbohydrate column), and then distilled water as a mobile phase was passed through at a speed of 0.5 ml/min. The enzyme unit is defined as an amount that produces 1 μmole of D-psicose per minute under conditions of pH 8.0 and 50° C.

Example 1

Preparation of D-Psicose 3-Epimerase Variant with Improved Thermostability by Random Mutagenesis A library of D-psicose 3-epimerase variant was constructed using, as a template, D-psicose 3-epimerase derived from *Agrobacterium tumefaciens* ATCC 33970 (having an amino acid sequence identical to that of SEQ ID NO: 1 disclosed in Korean Patent Publication No. 10-2011-0035805A) through error-prone polymerase chain reaction (error-prone PCR).

Specifically, a typical PCR mutagenesis kit causing two to three mutations per 1000 base pairs was employed. As a primer, an oligonucleotide to which sequences of restriction enzyme recognition sites of NcoI and PstI restriction enzymes were introduced was used to conduct polymerase chain reaction, thereby constructing a gene library encoding the D-psicose 3-epimerase variant, which was then inserted to *E. coli* BL21.

LB medium containing 50 μg/ml of ampicillin was used to culture *E. coli* BL21 including a plasmid in which a gene of a variant of the D-psicose 3-epimerase was introduced, followed by culturing at 37° C. for 6 hours. A portion was taken from the culture solution, transferred to a medium including 50 μg/ml of ampicillin and 0.1 mM of IPTG (Isopropyl-β-D-1-thiogalactopyranoside), and then cultured at 37° C. for 6 hours to induce expression of the enzyme. The cultured solution was heat treated at 60° C. for 5 minutes, followed by adding fructose so that the final concentration was 15 mM, and then reacted at 50° C. for 30 minutes. Then, using a general fructose assay kit, the residual amount of fructose was measured and 150 variants having activity about 1.2 times higher than the wide type enzyme were selected by comparing total 5000 variants with the wild type enzyme.

The selected 150 variants were induced to express enzymes again in the same manner as above. The cultured cells were subjected to ultrasonication to disrupt the cells. The disrupted cells were centrifuged to obtain a supernatant comprising D-psicose 3-epimerase. Then, the enzyme activity was measured using the above-mentioned "Method for measuring the activity of D-psicose 3-epimerase". As the result of measurement, 23 variants exhibiting high half-life at a reaction temperature of 55° C. were re-selected.

The genes of 23 re-selected variants were transferred from pTrc99A to pET-24a(+), which was used to transform *E. coli* BL21. The recombinant strain *E. coli* BL21 was cultured in LB medium containing 50 µg/ml of kanamycin at 37° C. When $OD_{600}$ reached 0.6, IPTG (Isopropyl-beta-thiogalactopyranoside) was added such that the final concentration was 0.1 mM, followed by culturing at 16° C. for 16 hours. The cultured solution was centrifuged to harvest bacterial components, which were then resuspended in 50 mM phosphate buffer solution including 300 mM KCl and 10 mM imidazole. The suspended solution was subjected to ultrasonication to crush the cells. The disrupted cell solution was centrifuged to harvest a supernatant including the D-psicose 3-epimerase, which was then purified using metal ion affinity chromatography. Imidazole in the purified enzyme was removed by employing a desalting cartridge.

The half-life of 23 re-selected variants was measured at 55° C. Five variants exhibiting the highest half-life were selected. The relative activity and half-life at 55° C. of the 5 selected variants and the wild type enzyme are summarized in Table 1.

TABLE 1

| D-psicose 3-epimerase | Relative activity (%) | Half-life (min) |
|---|---|---|
| Wild type | 100 ± 0.5 | 10 ± 2.3 |
| S8T | 29 ± 0.5 | 15 ± 0.3 |
| I33L | 88 ± 3.3 | 64 ± 0.2 |
| G67C | 8 ± 0.0 | 132 ± 0.4 |
| V96A | 51 ± 0.5 | 18 ± 0.2 |
| S213C | 103 ± 0.4 | 28 ± 0.7 |

As a result, of the half-lives were determined to be, in descending order, G67C>I33L>S213C>V96A>S8T. In view of half-life together with enzyme activity, two variants, I33L and S213C were identified as the most preferred variants.

The names for enzyme variants used herein were explained using I33L, for example. Number 33 means that an amino acid at position 33 of an amino acid sequence of a wild type D-psicose 3-epimerase is substituted, and the letters I and L at both sides of the number mean the initial letters of amino acids, respectively. To sum, I33L means that isoleucine (Ile) at position 33 of an amino acid sequence of D-psicose 3-epimerase is substituted with leucine (Leu).

Example 2

Preparation of D-Psicose 3-Epimerase Variant with Improved_Thermostability using Rational Design In a similar manner to Example 1, variants S213C and I33L were selected as variants having improved thermostability without significantly reducing activity. Based on the selected variants, site-directed mutagenesis was conducted at amino acids at positions 33 and 213 of the amino acid sequence.

Specifically, serine (Ser) at position 213 having polarity and no charge was substituted with threonine (Thr), cysteine (Cys) or methionine (Met) which has polarity and no charge; a proline (Pro) which is a non-polar amino acid; glutamic acid (Glu) which has a negative charge; and lysine (Lys) which has a positive charge, respectively.

Isoleucine at position 33 having no polarity was substituted with cysteine which has polarity and no charge; valine (Val), leucine or proline which is non-polar; glutamic acid which has a negative charge; and lysine having a positive charge, respectively.

Relative activity and half-life at 55° C. of the variants, amino acids of which were substituted as above, and the wild type enzyme were measured.

As a result, I33L, I33C, I33V and S213C variants having improved thermostability while not affecting the activity of the enzymes were obtained. Further, S213C variant was combined with I33L variant which was most preferred variant in view of enzyme activity and thermostability among the variants having an amino acid substituted at position 33 of the amino acid sequence, thereby obtaining a D-psicose 3-epimerase variant (I33L-S213C) having excellent activity and remarkably improved thermostability.

Table 2 summarizes the relative activity and half-life at 55° C. of the wild type D-psicose 3-epimerase derived from *Agrobacterium tumefaciens*, the variants in which an amino acid at position 33 or 213 is substituted, and the variants in which both amino acids at positions 33 and 213 are substituted.

TABLE 2

| D-psicose 3-epimerase | Relative activity (%) | Half-life (min) |
|---|---|---|
| Wild type | 100 ± 0.5 | 10 ± 2.3 |
| I33L | 88 ± 3.3 | 63 ± 0.2 |
| I33C | 83 ± 2.0 | 24 ± 0.6 |
| I33V | 92 ± 2.2 | 12 ± 0.4 |
| I33E | ND | ND |
| I33K | ND | ND |
| I33P | ND | ND |
| S213C | 103 ± 0.4 | 28 ± 0.7 |
| S213P | 95 ± 0.9 | 6 ± 0.2 |
| S213T | 68 ± 0.3 | 5 ± 0.1 |
| S213M | 22 ± 1.9 | 3 ± 0.3 |
| S213E | 19 ± 0.0 | 3 ± 0.1 |
| S213K | ND | ND |
| I33L-S213C | 74 ± 1.1 | 265 ± 2.3 |

ND: Not detectable

Comparative Experimental Example 1

Comparison of Apparent Melting Temperature of the Wild Type D-Psicose 3-Epimerase and D-Psicose 3-Epimerase Variants According to Example 2

In order to determine thermostability of the wild type D-psicose 3-epimerase and D-psicose 3-epimerase variants according to Example 2, that is, I33L, S213C and I33L-S213C, the apparent melting temperature ($T_m$) of each enzyme (or variant) was measured.

Figure 2:
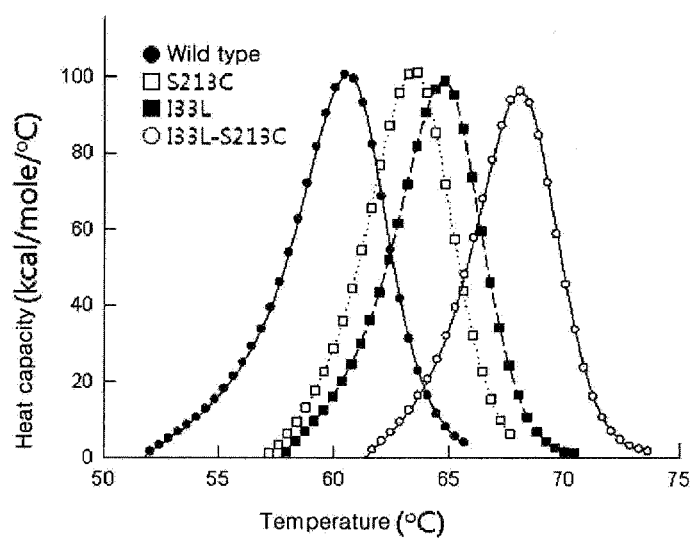
FIG. 2 is a graph depicting an apparent melting temperature profile of a wild type and variants (S213C, I33L, and I33L-S213C) of D-psicose 3-epimerase derived from *Agrobacterium tumefaciens* using DSC (differential scanning calorimeter). The peak portion of the graph represents an apparent melting temperature of the enzyme.

As a result, it could be seen that the apparent melting temperature was, in ascending order, wild type <S213C<I33L<I33L-S213C (FIG. 2). Specifically, as compared to the wild type, the apparent melting temperature was increased by about 4.3° C. in case of S213 variant, and by about 7.6° C. in case of I33L-S213C variant.

Comparative Experimental Example 2

Comparison of Enzyme Reaction Rate of the Wild Type D-Psicose 3-Ppimerase and D-Psicose 3-Epimerase Variants According to Example 2

In order to determine the enzyme reaction rate of the wild type D-psicose 3-epimerase and D-psicose 3-epimerase variants according to Example 2, namely, I33L, S213C and I33L-S213C, kinetic parameters of each enzyme (or variant) at a reaction temperature of 50° C. were observed.

The measurement results are summarized in Table 3.

TABLE 3

| D-psicose 3-epimerase | Km (mM) | $k_{cat}$ (min$^{-1}$) | $k_{cat}/K_m$ |
|---|---|---|---|
| Wild type | 44 ± 0.4 | 4338 ± 6 | 99 ± 0.9 |
| S213C | 42 ± 1.0 | 4194 ± 63 | 101 ± 3.0 |
| I33L | 40 ± 0.7 | 4240 ± 65 | 105 ± 2.5 |
| I33L-S213C | 31 ± 0.1 | 4135 ± 99 | 134 ± 3.2 |

As the result of measuring kinetic parameters of each enzyme, the wild type enzyme and variants I33L and S213C exhibited similar values, while I33L-S213C variant exhibited enzyme catalytic efficiency ($k_{cat}/K_m$), which was about 1.4 times greater than the wild type enzyme and variants I33L and S213C. This is because I33L-S213C forms an additional hydrogen bond as compared with other variants or the wild type enzyme, and a new stacking interaction between aromatic groups which cannot be found in the wild type enzyme, thereby forming a harder and denser structure, which in turn increases substrate affinity (FIG. 3).

Figure 3:
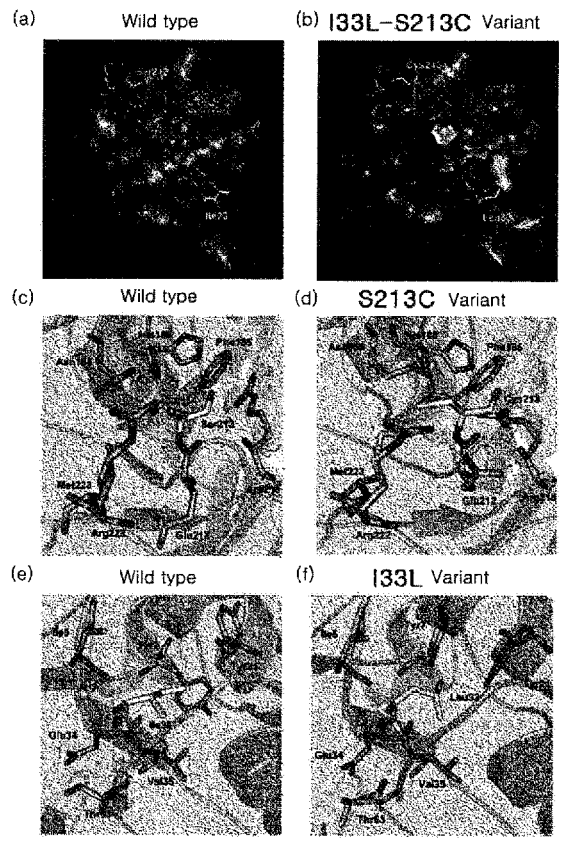
FIG. 3 depicts pictures of molecular modeling results of a wild type and variants (S213C, I33L, and I33L-S213C) of D-psicose 3-epimerase derived from *Agrobacterium tumefaciens*. (a) and (b) represent a secondary structure of the wild type and I33L-S213C variant, respectively. (c) and (d) represent estimated hydrogen bonds surrounding the amino acid at position 213 (serine (Ser) in case of wild type, and a cysteine (Cys) in case of S213C variant) of the amino acid sequence of the wild type and S213C variant, respectively. (e) and (f) represent interactions between aromatic groups of the wild type and I33L variant, respectively.

More specifically, in view of molecular modeling results, unlike the wild type enzyme having a serine at position 213 of the amino acid sequence and an isoleucine at position 33 of the amino acid sequence, which exist not at the active site but at the surface of the enzyme, it was found that I33L-S213C forms a coiled-coil interaction between cysteine at position 213 and leucine (Leu) at position 33 of the amino acid sequence (FIG. 3 (a), (b)). Such coiled-coil interaction is known to stabilize the structure of proteins.

Further, serine at position 213 of the amino acid sequence of the wild type enzyme is known to form two putative hydrogen bonds. However, for S213C wherein serine at position 213 of the amino acid sequence is substituted with cysteine, it could be seen that the putative hydrogen bonds were increased to six [FIG. 3 (c), (d)], which was also determined to make the structure of the protein denser, contributing to increase thermostability.

Further, in the molecular modeling, the wild type enzyme appears to have no interactions between aromatic groups. On the contrary, it could be seen that I33L variant exhibited stacking interactions between aromatic groups (FIG. 3 (e), (f)). It is determined that the stacking interaction between aromatic groups is a factor increasing thermostability.

Example 3

Preparation and Culturing of a Recombinant Strain Transformed with a recombinant Vector Including a Gene of I33L-S213C Variant According to Example 2

(1) Preparation of Recombinant Strain

A gene encoding D-psicose 3-epimerase was amplified through a polymerase chain reaction using DNA of I33L-S213C variant according to Example 2 as a template and an oligonucleotide to which sequences of recognition sites of PstI and XbaI restriction enzymes are introduced as a primer. In order to express the D-psicose 3-epimerase encoded by the amplified gene on large scale, a recombinant expression vector pFIs-1-ATPE-2 (FIG. 1) was constructed by inserting the amplified PCR product cut by restriction enzymes PstI and Xba I into a shuttle vector pCJ-1 (deposited at Korean Culture Center of Microorganisms (KCCM), which is international depository, on Nov. 6, 2004 as accession number KCCM-10611) derived from a bacteria belonging to genus *Corynebacterium*.

The recombinant expression vector was introduced into *Corynebacterium glutamicum* ATCC 13032 by transformation using electroporation to prepare a recombinant strain capable of expressing a gene encoding D-psicose 3-epimerase derived from *Agrobacterium tumefaciens*.

The recombinant strain was named *Corynebacterium glutamicum* pFIS-1-ATPE-2 and deposited at Korean Culture Center of Microorganisms (KCCM) on Aug. 18, 2011 as accession number KCCM 12204P.

(2) Culturing the Recombinant Strain

The recombinants strain obtained in (1) above was inoculated to a MB medium containing 10 μg/ml of kanamycin (10 g/L of Bacto-tryptone, 5 g/L of Bacto-yeast extract, 5 g/L of NaCl, 5 g/L of Soytone) at an initial concentration of $OD_{600}$=0.1, followed by culturing at 30° C. for 24 hours to induce the expression of D-psicose 3-epimerase variants. The obtained culture solution was inoculated to a fermenter charged with a mutation medium (8 g/L of glucose, 20 g/L of soytone, 10 g/L of $(NH_4)_2SO_4$, 1.2 g/L of $KH_2PO_4$, 1.4 g/L of $MgSO_4$) containing 10 μg/ml concentration of kanamycin at $OD_{600}$=0.6, cultured at 30° C. for 20 hours.

Example 4

Immobilization of Recombinant Strain According to Example 3 and Continuous Preparation of D-Psicose Through the Immobilized Reactor After culturing the recombinant strain according to Example 3, bacterial cells were harvested by centrifugation of the culture solution. The harvested cells were suspended in 50 mM EPPS buffer solution (pH 8.0) so that the concentration of the harvested cells is 20%. The bacterial cells of the suspended recombinant strain were added to an aqueous solution of 2% (v/v) sodium alginate. The mixed solution was added dropwise into 100 mM $CaCl_2$ solution by means of a syringe pump and a vacuum pump to generate bacterial cells-alginate conjugate wherein the bacterial cells were entrapped in a bead of sodium alginate. D-psicose was continuously prepared using an immobilized reactor formed by filling a packed bed column with the recombinant strain immobilized at sodium alginate.

Comparative Experimental Example 3

Comparison of operation stability of an immobilized reactor using $a_{13}$wild type D-psicose 3-epimerase and an immobilized reactor according to Example 4

In order to measure operation stability of an immobilized reactor using a wild type D-psicose 3-epimerase and an immobilized reactor according to Example 4, the reaction temperature was set to 50° C., and through the respective reactors, D-psicose was continuously prepared for two months, and then the activity of D-psicose was measured. The concentration of fructose was 480 g/L and flow rate was 850 ml/h.

Figure 4:
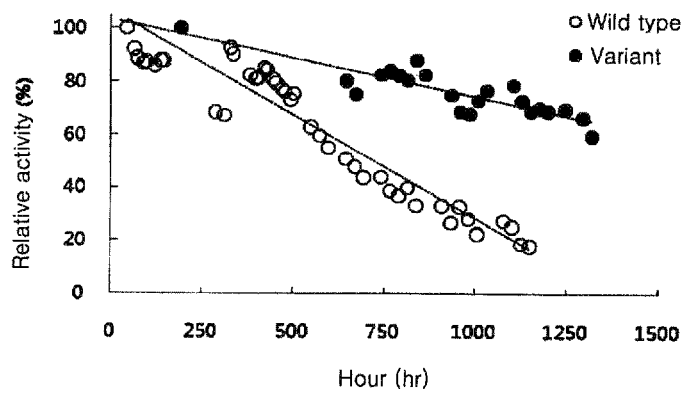
FIG. 4 is a graph depicting operation stability at a reaction temperature of 50° C. of an immobilized reactor using variants in a method according to one embodiment of the present invention.

As a result, as compared with an immobilized reactor using the wild type, it could be seen that the immobilized reactor using variants with improved thermostability and enzyme activity maintained high operation stability for more than two months. Specifically, the immobilized reactor using the wild type exhibited about 30 days of half-life, whereas the immobilized reactor using I33L-S213C variant exhibited a half-life of about 77 days (FIG. 4).

Therefore, it is expected that the enzymes according to the present invention can be used for a long time, thereby reducing production costs for D-psicose.

The invention claimed is:

1. A D-psicose 3-epimerase variant with improved thermostability, wherein the variant is a variant of a wild type D-psicose 3-epimerase of SEQ ID NO:1 derived from *Agrobacterium tumefaciens* and has an amino acid sequence in which isoleucine (Ile) at position 33 of the amino acid sequence of SEQ ID NO:1 is substituted with an amino acid selected from the group consisting of leucine (Leu), cysteine (Cys) and valine (Val), or an amino acid sequence in which serine (Ser) at position 213 of the amino acid sequence of SEQ ID NO:1 is substituted with cysteine.

2. A D-psicose 3-epimerase variant with improved thermostability, wherein the variant is a variant of a wild type D-psicose 3-epimerase of SEQ ID NO:1 derived from *Agrobacte-*

*rium tumefaciens* and has an amino acid sequence in which isoleucine (Ile) at position 33 of the amino acid sequence of SEQ ID NO:1 is substituted with an amino acid selected from the group consisting of leucine (Leu), cysteine (Cys) and valine (Val), and serine (Ser) at position 213 of the amino acid sequence of SEQ ID NO:1 is substituted with cysteine.

3. A recombinant expression vector comprising a gene encoding the D-psicose 3-epimerase variant according to claim 1.

4. A *Corynebacterium glutamicum* pFIS-1-ATPE-2 transformed with the recombinant expression vector according to claim 3.

5. A method of producing D-psicose from fructose, comprising producing D-psicose from fructose in the presence of the D-psicose 3-epimerase variant according to claim 1.

6. A method of producing a D-psicose from fructose, comprising producing a D-psicose from fructose in the presence of the recombinant *Corynebacterium glutamicum* pFIS-1-ATPE-2 according to claim 4.

7. An immobilized reactor for producing a D-psicose comprising a column filled with a carrier to which the D-psicose 3-epimerase variant according to claim 1 is immobilized.

8. A method of producing a D-psicose, comprising introducing a fructose solution into the immobilized reactor according to claim 7.

9. A recombinant expression vector comprising a gene encoding the D-psicose 3-epimerase variant according to claim 2.

10. A *Corynebacterium glutamicum* pFIS-1-ATPE-2 transformed with the recombinant expression vector according to claim 9.

11. A method of producing D-psicose from fructose, comprising producing D-psicose from fructose in the presence of the D-psicose 3-epimerase variant according to claim 2.

12. A method of producing a D-psicose from fructose, comprising producing D-psicose from fructose in the presence of the recombinant *Corynebacterium glutamicum* pFIS-1-ATPE-2 according to claim 10.

13. An immobilized reactor for producing a D-psicose comprising a column filled with a carrier to which the D-psicose 3-epimerase variant according to claim 2 is immobilized.

14. A method of producing a D-psicose, comprising introducing a fructose solution into the immobilized reactor according to claim 13.

* * * * *